(12) United States Patent
Madabhushi et al.

(10) Patent No.: US 10,492,723 B2
(45) Date of Patent: Dec. 3, 2019

(54) PREDICTING IMMUNOTHERAPY RESPONSE IN NON-SMALL CELL LUNG CANCER PATIENTS WITH QUANTITATIVE VESSEL TORTUOSITY

(71) Applicant: Case Western Reserve University, Cleveland, OH (US)

(72) Inventors: Anant Madabhushi, Shaker Heights, OH (US); Mehdi Alilou, Cleveland, OH (US); Vamsidhar Velcheti, Pepper Pike, OH (US)

(73) Assignee: Case Western Reserve University, Cleveland, OH (US)

( * ) Notice: Subject to any disclaimer, the term of this patent is extended or adjusted under 35 U.S.C. 154(b) by 93 days.

(21) Appl. No.: 15/883,649

(22) Filed: Jan. 30, 2018

(65) Prior Publication Data

US 2018/0242905 A1    Aug. 30, 2018

Related U.S. Application Data

(60) Provisional application No. 62/463,978, filed on Feb. 27, 2017.

(51) Int. Cl.
*A61B 5/00* (2006.01)
*G16H 30/40* (2018.01)
(Continued)

(52) U.S. Cl.
CPC ........ *A61B 5/4839* (2013.01); *A61B 5/02007* (2013.01); *A61B 5/4848* (2013.01);
(Continued)

(58) Field of Classification Search
CPC ....... G06T 7/0012; G06T 7/11; G06T 7/0016; G06T 2207/30101; G06T 2207/30064;
(Continued)

(56) References Cited

U.S. PATENT DOCUMENTS 9,092,691 B1    7/2015    Beaumont et al.
2003/0095692 A1    5/2003    Mundy et al.
(Continued)

OTHER PUBLICATIONS

Fraioli, et al. "CAD (Computed-Aided Detection) and CADx (Computer Aided Diagnosis) Systems in Identifying and Characterising Lung Nodules on Chest CT: Overview of Research, Developments and New Prospects." Radiol Med (2010) 115:385-402, published Jan. 15, 2010.
(Continued)

*Primary Examiner* — Brenda C Bernardi
(74) *Attorney, Agent, or Firm* — Eschweiler & Potashnik, LLC

(57) ABSTRACT

Embodiments classify a region of tissue demonstrating non-small cell lung cancer using quantified vessel tortuosity (QVT). One example apparatus includes annotation circuitry configured to segment a lung region from surrounding anatomy in the region of tissue represented in a radiological image and segment a nodule from the lung region by defining a nodule boundary; vascular segmentation circuitry configured to generate a three dimensional (3D) segmented vasculature by segmenting a vessel associated with the nodule, and to identify a center line of the 3D segmented vasculature; QVT feature extraction circuitry configured to extract a set of QVT features from the radiological image; and classification circuitry configured to compute a probability that the region of tissue will respond to immunotherapy and generate a classification that the region of tissue is a responder or a non-responder based, at least in part, on the probability.

20 Claims, 7 Drawing Sheets

(51) Int. Cl.
| | |
|---|---|
| *G16H 20/40* | (2018.01) |
| *G06K 9/62* | (2006.01) |
| *G06T 7/11* | (2017.01) |
| *G06T 7/00* | (2017.01) |
| *G16H 50/20* | (2018.01) |
| *A61B 6/03* | (2006.01) |
| *A61B 6/00* | (2006.01) |
| *A61B 5/02* | (2006.01) |
| *G16H 50/30* | (2018.01) |
| *G16H 50/50* | (2018.01) |
| *A61B 5/055* | (2006.01) |
| *G06K 9/00* | (2006.01) |

(52) U.S. Cl.
CPC ............ *A61B 6/032* (2013.01); *A61B 6/504* (2013.01); *A61B 6/5217* (2013.01); *G06K 9/6262* (2013.01); *G06K 9/6268* (2013.01); *G06T 7/0012* (2013.01); *G06T 7/0016* (2013.01); *G06T 7/11* (2017.01); *G16H 20/40* (2018.01); *G16H 30/40* (2018.01); *G16H 50/20* (2018.01); *G16H 50/30* (2018.01); *G16H 50/50* (2018.01); *A61B 5/055* (2013.01); *A61B 5/4842* (2013.01); *A61B 5/7264* (2013.01); *G06K 2009/00932* (2013.01); *G06K 2009/6213* (2013.01); *G06K 2209/051* (2013.01); *G06K 2209/053* (2013.01); *G06T 2207/10081* (2013.01); *G06T 2207/20081* (2013.01); *G06T 2207/30064* (2013.01); *G06T 2207/30101* (2013.01); *G06T 2207/30172* (2013.01)

(58) Field of Classification Search
CPC . G06T 2207/20081; G06T 2207/10081; G06T 2207/30172; A61B 5/4839; A61B 6/032; A61B 6/504; A61B 6/5217; A61B 5/02007; A61B 5/4848; A61B 5/055; A61B 5/7264; A61B 5/4842; G16H 30/40; G16H 20/40; G16H 50/20; G16H 50/30; G16H 50/50; G06K 9/6262; G06K 9/6268; G06K 2209/051; G06K 2009/6213; G06K 2209/053; G06K 2009/00932
See application file for complete search history.

(56) References Cited

U.S. PATENT DOCUMENTS

| | | |
|---|---|---|
| 2004/0252870 A1 | 12/2004 | Reeves et al. |
| 2005/0207630 A1 | 9/2005 | Chan et al. |
| 2007/0019846 A1* | 1/2007 | Bullitt .................. G06T 7/0014 |
| | | 382/128 |
| 2007/0081712 A1 | 4/2007 | Huang et al. |
| 2008/0002870 A1 | 1/2008 | Farag et al. |
| 2008/0205717 A1 | 8/2008 | Reeves et al. |
| 2009/0005693 A1 | 1/2009 | Brauner et al. |
| 2010/0111386 A1 | 5/2010 | El-Baz |
| 2010/0323903 A1 | 12/2010 | Rosenwald et al. |
| 2012/0150048 A1 | 6/2012 | Kang et al. |
| 2013/0217956 A1 | 8/2013 | Thompson et al. |
| 2013/0225662 A1 | 8/2013 | Kennedy et al. |
| 2013/0259345 A1 | 10/2013 | El-Baz et al. |
| 2016/0110632 A1 | 4/2016 | Kiraly et al. |
| 2016/0155225 A1* | 6/2016 | Madabhushi ......... G06T 7/0012 |
| | | 382/131 |
| 2016/0239956 A1* | 8/2016 | Kang ..................... G06T 17/005 |
| 2017/0035381 A1* | 2/2017 | Madabhushi ........ A61B 5/7267 |
| 2017/0039737 A1 | 2/2017 | Madabhushi et al. |

OTHER PUBLICATIONS

Awai, et al. "Pulmonary Nodules: Estimation of Malignancy at Thin-Section Helical CT—Effect of Computer-aided Diagnosis on Performance of Radiologists." Radiology: vol. 239: No. 1, Apr. 2006.
Ko, et al. "Lung Adenocarcinoma: Correlation of Quantitative CT Findings with Pathologic Findings." Radiology: vol. 280: No. 3, Sep. 2016.
Aoyama, et al. "Computerized Scheme for Determination of the Likelihood Measure of Malignancy for Pulmonary Nodules on Low-Dose CT Images." Med. Phys. 30 (3), Mar. 2003.
U.S. Appl. No. 15/226,124, filed Aug. 2, 2016.
Non-Final Office Action dated Oct. 30, 2017 for U.S. Appl. No. 15/226,124.
U.S. Appl. No. 15/226,148, filed Aug. 2, 2016.
Non-Final Office Action dated Oct. 30, 2017 for U.S. Appl. No. 15/226,148.
Notice of Allowance dated Apr. 16, 2019 for U.S. Appl. No. 15/937,105.
U.S. Appl. No. 15/937,105, filed Mar. 27, 2018.
U.S. Appl. No. 16/043,498, filed Jul. 24, 2018.
Notice of Allowance dated May 2, 2018 for U.S. Application No. 15/226,124.

* cited by examiner

US 10,492,723 B2

PREDICTING IMMUNOTHERAPY RESPONSE IN NON-SMALL CELL LUNG CANCER PATIENTS WITH QUANTITATIVE VESSEL TORTUOSITY

CROSS REFERENCE TO RELATED APPLICATIONS

This application claims the benefit of U.S. Provisional Application 62/463,978, filed Feb. 27, 2017.

FEDERAL FUNDING NOTICE

The invention was made with government support under the National Cancer Institute of the National Institutes of Health under award numbers 1U24CA199374-01, R01CA202752-01A1, R01CA208236-01A1, R21CA179327-01, R21CA195152-01, the National Institute of Diabetes and Digestive and Kidney Diseases under award number R01DK098503-02, National Center for Research Resources under award number 1 C06 RR12463-01, the DOD Prostate Cancer Synergistic Idea Development Award (PC120857), the DOD Lung Cancer Idea Development New Investigator Award (LC130463), the DOD Prostate Cancer Idea Development Award, and the DOD Peer Reviewed Cancer Research Program W81XWH-16-1-0329. The government has certain rights in the invention.

BACKGROUND

Variations of lung nodule invasiveness and morphology relate to patient response to immunotherapy. One approach for predicting response to immunotherapy is histopathological examination of biopsy tissue. The examination may produce a profile based on attributes including cell morphology, cytoplasmic changes, cell density, or cell distribution. Biopsy is invasive, and visual characterization of tumor morphology is time consuming and expensive. Visual characterization is also subjective and thus suffers from inter-rater and intra-rater variability. Conventional visual characterization of nodule morphology by a human pathologist or radiologist may therefore be less than optimal in clinical situations where timely and accurate classification can affect patient outcomes.

Computed tomography (CT) is frequently used to image nodules or other regions of interest. For example, chest CT imagery may be used to detect and diagnose non-small cell lung cancer (NSCLC). However, conventional approaches to analyzing chest CT imagery have been challenged when attempting to distinguish NSCLC patients who will respond to immunotherapy from NSCLC patients who will not respond to immunotherapy. Immunotherapy may include immune-checkpoint blockade treatments, including drugs that target the programmed death-1 (PD-1) receptor. While drugs that target the PD-1 pathway in NSCLC may have some efficacy in treating NSCLC, the dynamic and complex nature of the host-immune responses make tissue-based biomarker development for predicting patient response to immunotherapy drugs difficult.

Since radiologists using conventional CT approaches may be challenged to reliably discriminate in clinically optimal or relevant time frames between NSCLC patients that will respond to immunotherapy from those who will not respond to immunotherapy, NSCLC patients may be subjected to treatments that are inconvenient, invasive, expensive, or unhelpful. For example, many NSCLC patients who will not respond to immunotherapy are nevertheless subjected to immunotherapy.

Immunotherapy takes time, costs money, and may put a patient at additional risk. As the number of routine chest CT scans increases with the wide-spread adoption of CT-based lung cancer screening protocols, it would be beneficial to reduce unnecessary application of immunotherapy to patients who will not benefit from it.

BRIEF DESCRIPTION OF THE DRAWINGS

The accompanying drawings, which are incorporated in and constitute a part of the specification, illustrate various example apparatus, methods, systems, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
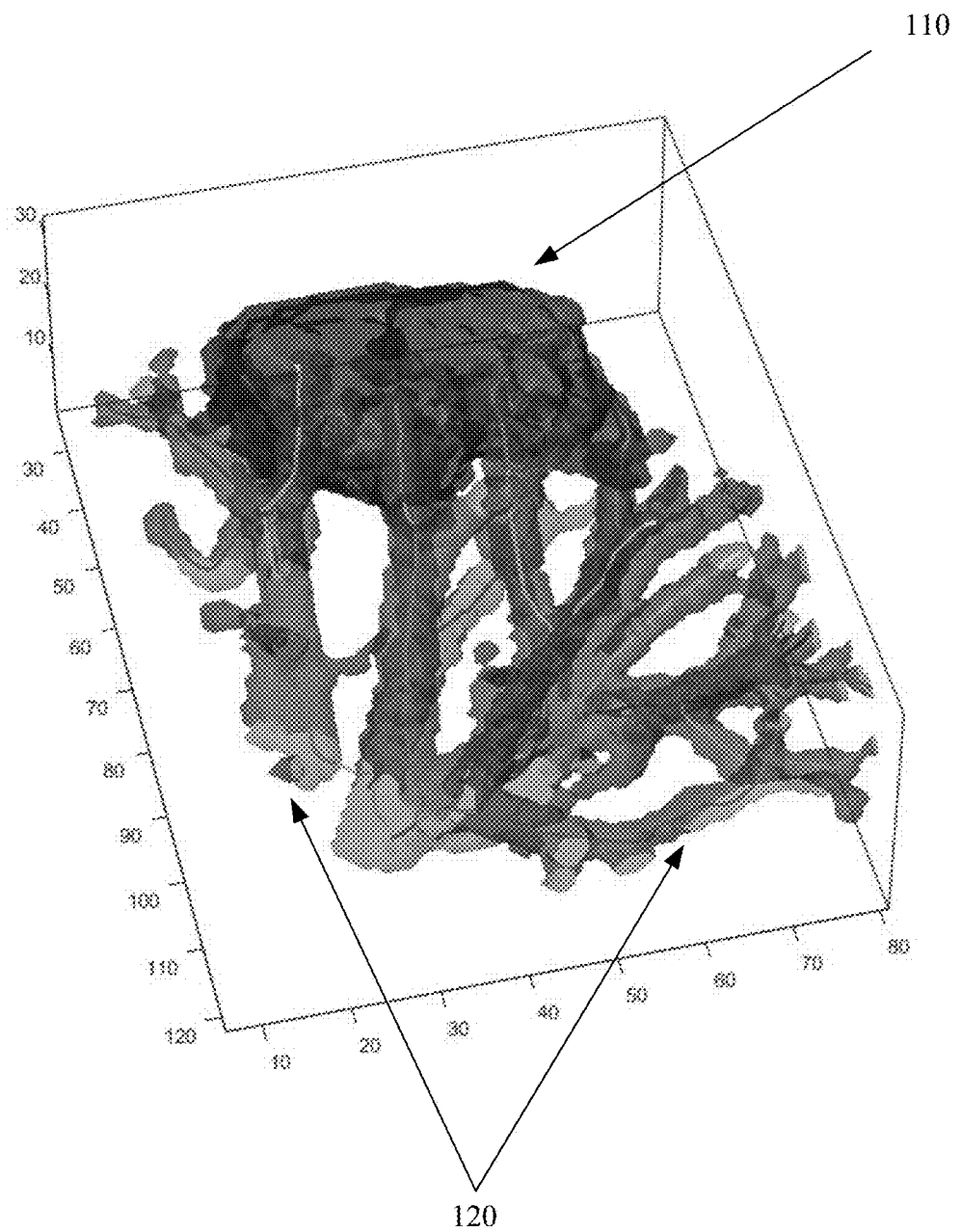
FIG. 1 illustrates an example three dimensional (3D) segmented vasculature.

Immune-checkpoint blockade treatments, including drugs that target the PD-1 receptor, demonstrate clinical efficacy in some patients with NSCLC. However, the efficacy of many drugs that target the PD-1 pathway or the related programmed death-ligand 1 (PD-L1) pathway may be modest in some patients. The dynamic and complex nature of the host-immune responses makes tissue-based biomarker development for predicting patient response to immunotherapy drugs challenging. A non-invasive approach that provided improved accuracy compared to conventional CT-based approaches would reduce the number of unnecessary interventions, reduce the dependency on repetitive or higher radiation radiological exams, offer a non-invasive means of predicting response to targeted therapies, and improve patient outcomes. Thus, a timely, less expensive, non-invasive procedure that results in more accurate discrimination between responders and non-responders to immunotherapy, or that more accurately predicts a response to immunotherapy, would offer reduced risk and improved outcomes to patients while providing economic benefits to the health care system.

CT imagery is conventionally used to differentiate malignant nodules from other, non-cancerous or non-pathological nodules. A nodule may be, for example, a tumor, a ground glass opacity (GGO) nodule, or a solitary pulmonary nodule. However, it is difficult to distinguish nodules in patients who will respond to immunotherapy from patients who will not respond to immunotherapy, since nodules in both classes of patient (e.g. responder, non-responder) can have similar appearances on CT evaluation. For example, on chest a CT image, nodules in a patient that will respond to immunotherapy may have similar visual characteristics to nodules in a patient that will not respond to immunotherapy. Furthermore, the tortuosity of vessels in or associated with a tumor or nodule may differ between responders and non-responders, yet this difference may be undetectable to the human eye.

Embodiments described herein differentiate NSCLC patients who will respond to immunotherapy, including PD-1 inhibitor immunotherapy or PD-L1 inhibitor immunotherapy, from NSCLC patients who will not respond to immunotherapy, by extracting and analyzing quantitative measurements of the tortuosity of vessels associated with a lung nodule represented in a CT image of a patient. The CT image may be a baseline pre-treatment (e.g. pre-administration of immunotherapy) CT image, or a post-treatment (e.g. post-administration of immunotherapy) CT image.

The vasculature associated with malignancy is abnormally shaped. Dysregulation of angiogenesis is a hallmark of solid tumors. An imbalance of pre-angiogenic and anti-angiogenic signaling within tumors creates an abnormal vascular network. This abnormal vascular network may be characterized by dilated, tortuous, or hyperpermeable vessels. These abnormalities and the resultant microenvironment fuel tumor progression. These abnormalities and the resultant microenvironment also lead to a reduction in the efficacy of immunotherapy and chemotherapy.

Malignancy makes regional changes to vessel shape and tortuosity. Tortuosity abnormalities appear during the tumor development process and affect initially healthy vessels which are spread beyond the confines of the tumor or tumor margins. The tortuosity of vessels in a tumor or nodule, or in the tumor's neighborhood (e.g. perinodular zone) contains prognostic information that facilitates discriminating responders from non-responders. The tortuosity of vessels of a nodule is also associated with underlying gene-expression patterns. Thus, the tortuosity of vessels in a tumor, nodule, or other region of tissue (e.g. perinodular zone) associated with the tumor or nodule may be used by example methods and apparatus to facilitate supporting decisions made to predict patient response to immunotherapy. Example methods and apparatus distinguish patients who will respond to immunotherapy from patients who will not respond to immunotherapy, and provide decision support in the diagnosis and treatment of patients exhibiting lung nodules in radiological imagery. Distinguishing responders from non-responders facilitates reducing the application of immunotherapy to patients who are unlikely to benefit from immunotherapy, and directing the application of immunotherapy to patients who are more likely to benefit.

Example methods and apparatus more accurately distinguish patients who will respond to immunotherapy from patients who will not respond to immunotherapy by extracting and analyzing a set of tortuosity features from a lung nodule or region of tissue associated with the nodule represented in a radiological image. The set of tortuosity features captures vascular curvature, branching statistics, and tortuosity characteristics of vessels associated with the nodule. Tortuosity features, compared to other features employed by conventional approaches, are intensity invariant, and do not exhibit sensitivity to imaging parameters such as scale or resolution that makes conventional approaches sub-optimal. Since a more accurate distinction is made, example apparatus and methods thus predict patient outcomes in a more consistent and reproducible manner than conventional approaches.

In one embodiment, members of an initial cohort of a total of 61 NSCLC patients who underwent immunotherapy treatment are classified as responders or non-responders. In this example, patients who did not receive nivolumab after two cycles of immunotherapy treatment due to lack of response or progression as per response evaluation criteria in solid tumors (RECIST) are classified as 'non-responders'. Patients who had radiological response as per RECIST, or stable disease as per RECIST and clinical improvement, are classified as 'responders'. A training cohort including CT images of 33 patients along with their corresponding response to therapy is selected from the initial cohort. A blinded validation cohort of CT scans from the other 28 patients is selected from the initial cohort. The blinded validation cohort and the training cohort are disjoint. While a total of 61 NSCLC patients are described in this example, the initial cohort may include another different number of patients. Similarly, the training cohort and blinded validation cohort may include other different numbers of patients.

In this example, lung nodules on pre-treatment CT scans are annotated on 3D-Slicer software. A total of 35 quantitative tortuosity features of the vessels associated with lung nodule were investigated for inclusion in a set of quantitative vessel tortuosity (QVT) features. A minimally-interactive 3D click and grow algorithm was employed to segment the vasculature associated with the nodules. A fast marching algorithm was employed to identify the center lines of the 3D segmented vasculature. The tortuosity features extracted from center lines capture the curvature, tortuosity, and branching statistics of the vasculature associated with the nodules. In the training cohort, the extracted features were evaluated and ranked by their ability to discriminate responders to immunotherapy using a machine learning classifier, both in terms of univariate and multivariate analysis. The three most informative features were selected and used for training a support vector machine (SVM) classifier. Finally, the SVM was applied to the blinded validation cohort to predict the possible responders to immunotherapy.

In this example, the maximum curvature of vessels branch (f1), standard deviation of the vessels torsion (f2) and mean curvature (f3) were identified as the most discriminating features. The area under receiver operating characteristic (ROC) curve of the machine learning classifier is at least an AUC=0.84±0.04 for the training cohort. The independent validation of the blinded validation cohort yields an AUC of at least 0.72. This is a substantial and measurable improvement over conventional approaches to predicting response to immunotherapy, such as PDL1 expression, which achieves results no better than random guessing.

In one embodiment, the nodule may be segmented from the image background using a spectral embedding gradient vector flow active contour (SEGvAC) model, or other segmentation approach. A region associated with the nodule may be defined with respect to the nodule segmented from the image background. The region associated with the nodule may extend a threshold distance from the nodule boundary as determined by the segmentation of the nodule from the image background, or may be defined using other approaches. A set of tortuosity features may be extracted from the nodule or the region associated with the nodule. Example methods and apparatus also detect and quantify differences in lymphatic vessel density within the region associated with the nodule. Features, including QVT features, extracted from the nodule or the region associated with the nodule may facilitate improved detection and analysis of histologic patterns demonstrated by NSCLC, including lepidic patterns, acinar patterns, papillary patterns, micropapillary patterns, or solid patterns. Features extracted from the region associated with the nodule or the nodule may facilitate capturing growth patterns of NSCLC or other malignancies, including angiogenesis, tumor growth, invasion, or metastasis that constitute a neoplastic microenvironment around the nodule. A subset of extracted tortuosity features may be selected using principal component analysis (PCA)-variable importance projection (VIP) or other technique. The subset of extracted features may include tortuosity features that are more discriminative than other, non-selected features. The subset may have a lesser cardinality that the initial set of tortuosity features. A classification of the nodule represented in the image may be generated using quadratic discriminant analysis (QDA), linear discriminant analysis (LDA), or other analysis technique.

Example methods and apparatus may train and test a machine learning classifier to predict response to immunotherapy or to compute a probability that a region of tissue or patient will respond to immunotherapy. For example, one embodiment may employ 3-fold cross validation to train a classifier and to test the classifier. The classifier may be a support vector machine (SVM) classifier or other type of machine learning classifier, including a QDA classifier, and LDA classifier, or a convolutional neural network (CNN). For example, a human radiologist may manually delineate and classify nodules in images of thirty three patients already identified as responders or non-responders for a training set and images of twenty-eight patients already identified as responders or non-responders for a testing set. Example embodiments may classify the patient or the nodule represented in the image as a responder or non-responder. In other embodiments, other classification schemes may be employed. For example, a nodule may be classified as a "responder", "non-responder", or "unknown response". Other sizes of training sets or sizes of testing sets may be employed. Example methods and apparatus may also classify the nodule as having a threshold probability of responding to treatment.

Example methods and apparatus may employ an SVM classifier in conjunction with PCA-VIP determined features to discriminate responders from non-responders. The classifier may be trained solely on the training set. A radial-based kernel function (RBF) may be applied to the training set. Members of the training set are defined in instance-label form $(x_i, y_i)$ where $x_i \in R^n$ and $y_i \in \{-1, 1\}$. The RBF function is formally defined as:

$$K(x_i, x_j) = \exp(\gamma \|x_i - x_j\|^2), \gamma > 0.$$

In another embodiment, the machine learning classifier may be trained using other machine learning techniques. Example embodiments thus improve on conventional methods by more accurately distinguishing between responders and non-responders. Example embodiments distinguish responders from non-responders with an accuracy of at least 0.72 AUC. By increasing the accuracy with which responders are distinguished from non-responders, or by which response to treatment is predicted, example embodiments described herein produce the concrete, real-world technical effect of reducing the time required to evaluate medical imagery while increasing the accuracy of the evaluation. Additionally, example apparatus and methods increase the probability that at-risk patients receive timely treatment tailored to the particular pathology they exhibit. Example methods and apparatus may also reduce the amount of ineffective immunotherapy applied to patients. The additional technical effect of reducing the expenditure of resources and time on patients who are less likely to suffer recurrence or disease progression is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 3:
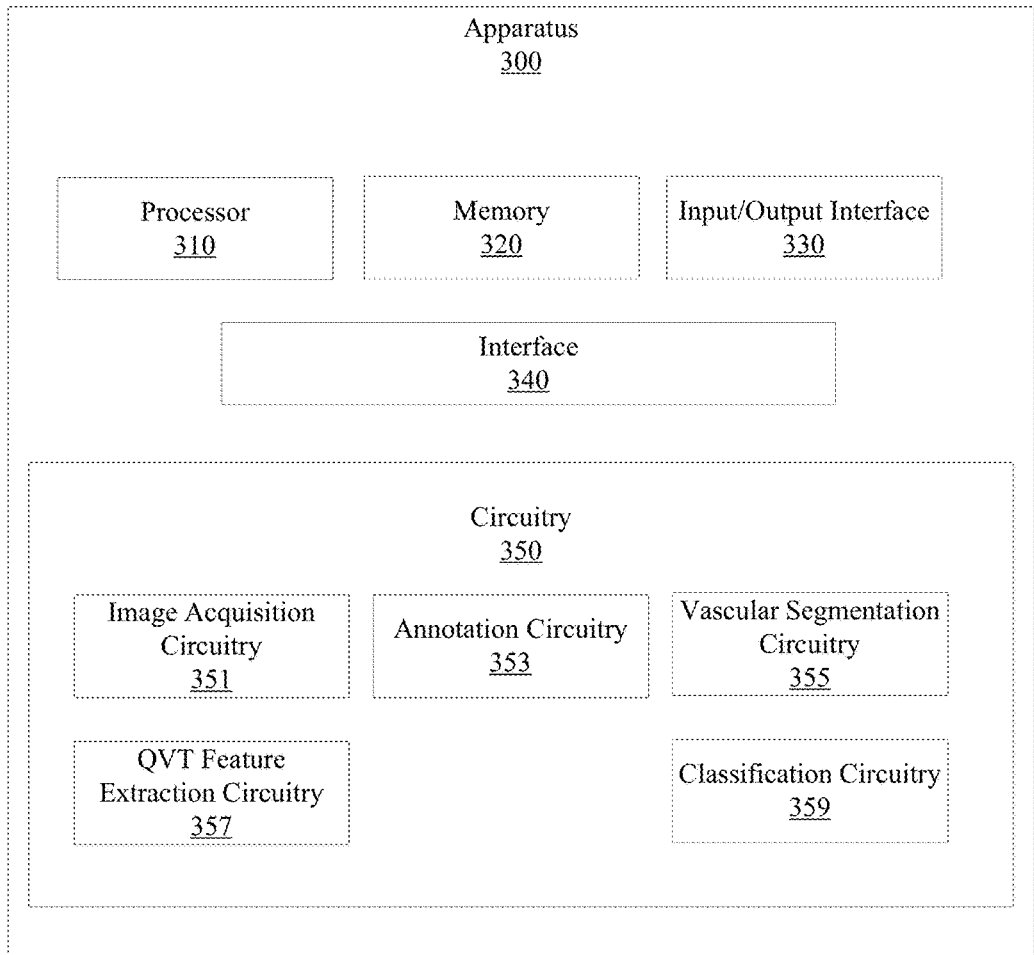
FIG. 3 illustrates an example apparatus for predicting response to immunotherapy.

FIG. 3 illustrates an immunotherapy response prediction apparatus 300. Immunotherapy response prediction apparatus 300 is configured to generate a classification of a region of tissue demonstrating NSCLC based on a set of QVT features extracted from a radiological image of the region of tissue. Immunotherapy response prediction apparatus 300 is configured to classify the region of tissue, or the patient from which the radiological image of the region of tissue was acquired, as a responder or non-responder. Immunotherapy response prediction apparatus 300 includes a processor 310, a memory 320, an input/output (I/O) interface 330, a set of circuitry 350, and an interface 340 to connect the processor 310, the memory 320, the I/O interface 330, and the set of circuitry 350. In one embodiment, memory 320 is configured to store an electronic copy of the radiological image of the region of tissue.

In one embodiment, the set of circuitry 350 includes image acquisition circuitry 351, annotation circuitry 353, vascular segmentation circuitry 355, QVT feature extraction circuitry 357, and classification circuitry 359. In one embodiment, the functionality associated with the set of circuitry 350 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuitry 350 are implemented as ASICs or SOCs.

Image acquisition circuitry 351 is configured to access a radiological image of a region of tissue demonstrating NSCLC. In one embodiment, accessing the radiological image includes accessing a CT image of region of lung tissue. The radiological image may be acquired from, for example, a CT apparatus. The radiological image includes a plurality of voxels, a voxel having an intensity. In one embodiment, the CT image is a no-contrast chest CT image. In one embodiment, the CT image is a baseline pre-treatment CT image. The baseline pre-treatment CT image is acquired of a patient demonstrating NSCLC before the administration of immunotherapy treatment to the patient. In another embodiment, the CT image is a post-treatment CT image. The post-treatment CT image is acquired a threshold time after the administration of immunotherapy treatment to the patient. In one embodiment, the threshold time is two weeks. For example, in this embodiment, the post-treatment CT image is acquired two weeks after the administration of immunotherapy treatment to the patient. In another embodiment, the threshold time may be three weeks, or another, different value. Accessing the radiological image may include retrieving electronic data from a computer memory, including memory 320, receiving a computer file over a computer network, or other computer or electronic based action.

In one embodiment, the radiological image is a 1 mm to 5 mm thick, no-contrast chest CT image. In one embodiment, the number of slices per scan may range from 126 to 385, and a slice may have an XY planar resolution of 512 pixels by 512 pixels, with a 16 bit gray scale resolution indicated in Hounsfield Units (HU). In another embodiment, other image types, modalities, resolutions, scales, slices per scan, or image dimensions may be used. For example, the radiological image may be a magnetic resonance imaging (MRI) image, including a dynamic contrast enhanced (DCE) MRI image.

Annotation circuitry 353 is configured to segment a lung region from surrounding anatomy in the region of tissue represented in the radiological image. In one embodiment, annotation circuitry 353 is configured to segment the lung region from surrounding anatomy in the region of tissue represented in the radiological image by distinguishing the lung region from the surrounding anatomy using a multi-threshold based approach or a heuristic threshold based approach. For instance, appropriate thresholds to distinguish the lung region from the surrounding anatomy could be optimally learnt from a set of training images. In other embodiments, annotation circuitry 353 is configured to segment the lung region from the surrounding anatomy using other, different approaches. In still other embodiments, other types or regions of tissue (e.g. breast, brain, prostate, rectal) may be segmented from surrounding anatomy.

Annotation circuitry 353 is further configured to segment a nodule from the lung region by defining a nodule boundary. In one embodiment, annotation circuitry 353 is configured to segment the nodule from the lung region by defining the nodule boundary by distinguishing nodule tissue in the radiological image from the background of the radiological image using a spectral embedding gradient vector flow active contour (SEGvAC) approach. In another embodiment, annotation circuitry 353 is configured to distinguish nodule tissue in the radiological image from the background of the radiological image using a heuristic threshold approach, threshold based segmentation, deformable boundary models, active-appearance models, active shape models, graph based models including Markov random fields (MRF), min-max cut approaches, or other image segmentation approaches. In another embodiment, the nodule may be manually segmented using, for example, a 3D Slicer software tool.

In one embodiment, a SEGvAC segmentation approach includes using a non-linear embedding representation of the lung to separate the image of the lung from the surrounding thoracic anatomy. The SEGvAC approach also includes removing non-nodule structures from the image using a rule-based classifier. The SEGvAC approach further includes extracting the nodule surface from the image using active contour based segmentation. Example embodiments employing a SEGvAC approach improve on conventional approaches by eliminating segmentation errors caused by both pleura and vessel attached nodules by separating lung tissues and removing non-nodule structures. Reducing such errors may increase the accuracy and/or speed with which example embodiments may classify tissue compared to conventional approaches.

SEGvAC segmentation employs a spectral embedding based active contour. Spectral embedding (SE) is a non-linear dimensional reduction method that forms an affinity matrix via a pre-specified kernel function. The kernel function facilitates a mapping of an original set of image features or intensities to a new kernel space where spectral decomposition may be applied to the corresponding graph Laplacian. An individual pixel or voxel from the original lung CT image (e.g. the radiological image) is then represented by the corresponding value of the eigenvectors obtained by spectral decomposition. SE representation of the lung provides strong gradients at the margin of the nodules which facilitate an active contour model to stop evolving at the nodule boundary. The SEGvAC approach employed by example methods and apparatus further includes a gradient vector flow field (GVF) active contour. The GVF forces are calculated for the image domain. The GVF forces drive the active contour.

In one embodiment, the SEGvAC segmentation approach includes isolating lung regions from surrounding anatomy illustrated in the CT image to generate an initial lung mask. Example embodiments identify an optimal threshold to separate body voxels from non-body voxels. A non-body voxel is a low density voxel representing lung and surrounding air. The initial lung mask is further refined by applying morphological hole filling to the logical complement of the initial lung mask.

Upon extraction of the initial region of interest (e.g. lung region) from the CT image, example methods and apparatus may perform an automatic segmentation of the nodule. Example embodiments employ an active contour scheme to segment the nodule. In one embodiment, the image plane $\Omega=R^2$ is partitioned into two regions by a curve $\gamma$. The foreground region of the image plane is defined as $\Omega_1$ and the background region of the image plane is defined as $\Omega_2$. Thus, the image plane is comprised of the union of regions of interest, background, and evolving contour $(\Omega=\Omega_1 \cup \Omega_2 \cup \gamma)$.

In simplified form, the energy functional of an edge-based active contour is defined as $$E = \alpha E_1 + \beta E_2 \quad (eq. 1)$$

where $E_2$ refers to internal forces used to keep the integrity and elasticity of the contour and where $E_1$ is the image force.

The image force $E_1$ is defined as $$E_1 = \int_x g(v(c))dc \quad (eq. 2)$$

where $c=(x,y)$ corresponds to a voxel in the two dimensional (2D) image plane, $v(c)$ is the intensity value of the voxel c, and $g(v(c))$ is defined as $$g(v(c)) = \frac{1}{1 + \psi(v(c))}. \quad (eq. 3)$$

The gradient function $\psi(v(c))$ is conventionally calculated by a gray level gradient. Example embodiments employ a tensor gradient function derived from the SE representation. By using the tensor gradient function, example embodiments facilitate the generation of improved region and boundary-based statistics, and stronger gradients, compared to conventional approaches.

Example embodiments employ a GVF active contour. The GVF forces calculated for the image domain are used to drive the active contour. Active contours driven by GVF forces do not need to be initialized very closely to the boundary. The GVF forces are calculated by applying generalized diffusion equations to both components of the gradient of an image edge map, where the image edge map is of the original CT image. In one embodiment, the SEGvAC approach is initialized using a single point and click on a region of interest (e.g. nodule, tumor). In another embodiment, the SEGvAC approach may be initialized automatically.

In one embodiment, before employing the SEGvAC approach, example methods and apparatus may employ a rule-based classifier to remove unwanted structures from the image based on geometric properties of the unwanted structures. The geometric properties of the unwanted structures may be 3D geometric properties. The 3D geometric properties may include bounding box measures and elongation of 3D structures defined as the length of the major axis of the nodule divided by the length of the minor axis of the nodule. Lung nodules are frequently 5 mm to 30 mm long. Thus, 3D structures that do not fit this size may be eliminated using the rule-based classifier. Candidate objects for inclusion or exclusion may be examined in terms of convexity or elongation measures for distinguishing vessel-like structures from more convex or sphere-like objects. In one embodiment, a set of morphological operations, including erosion and closing operations, may be employed to filter objects associated with vessel-connected nodules. Removing unwanted structures improves the performance of systems and devices employing example embodiments by reducing the computational complexity required to accurately characterize a tumor, nodule, or other region of tissue, compared to conventional approaches.

Vascular segmentation circuitry 355 is configured to generate a 3D segmented vasculature by segmenting a vessel associated with the nodule from the nodule. FIG. 1 illustrates an example nodule 110 and a 3D segmented vasculature 120. In one embodiment, vascular segmentation circuitry 355 segments the vessel from the nodule using a 3D click and grow approach. The 3D click and grow approach includes, in this embodiment, identifying a plurality of seed points within a volume of interest. A member of the plurality of seed points has an intensity. The volume of interest may be in the nodule, or the volume interest may include a region associated with the nodule. For example, the volume of interest may include a spherical volume extending a threshold distance from the centroid of the nodule. The 3D click and grow approach further includes computing an intensity similarity between a first member of the plurality of seed points and a second, different member of the plurality of seed points. The 3D click and grow approach also includes growing the volume of interest using a 3D region growing approach based, at least in part, on the intensity similarity. In another embodiment, vascular segmentation circuitry 355 segments the vessel from the nodule using a different segmentation approach. For example, vascular segmentation circuitry 355 may be configured to segment the vessel using an atlas based approach, a watershed based segmentation approach, or an active contour based method.

In one embodiment, the volume of interest may be defined as a function of a property of the nodule. The property of the nodule may include, for example, a diameter, a radius, a perimeter, an area, a volume, or other property of the nodule. The function may define the volume of interest as, for example, a dilation of the nodule boundary, where the dilation ratio is defined by a magnitude of an axis of the nodule. In another embodiment, the volume of interest may be defined as a disc of a threshold radius defined about the centroid of the nodule, or defined on the focal points of an elliptical representation of the nodule. In one embodiment, the volume of interest may be manually defined. Other approaches or combinations of approaches may be used to define the volume of interest.

Figure 2:
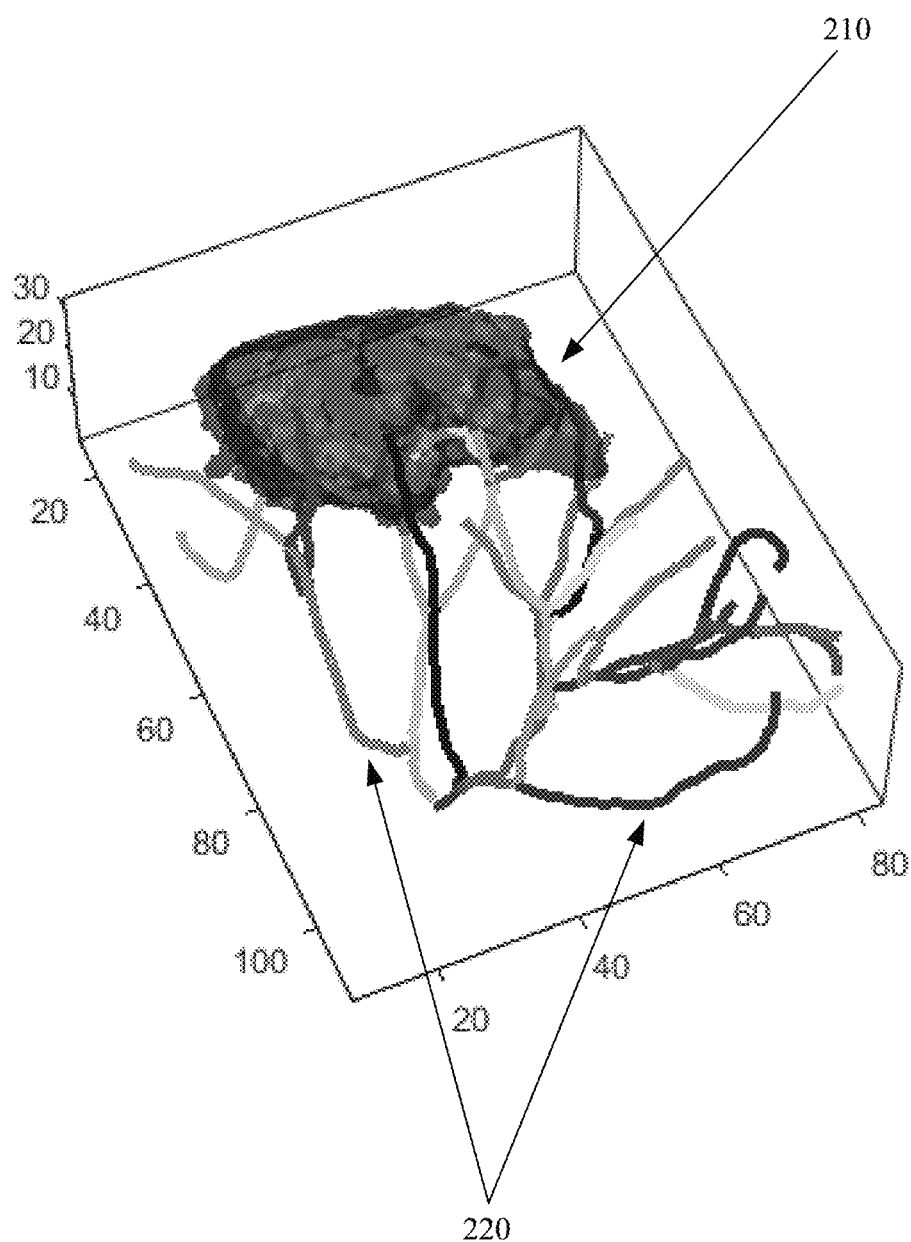
FIG. 2 illustrates centerlines of an example 3D segmented vasculature.

Vascular segmentation circuitry 355 is further configured to identify a center line of the 3D segmented vasculature. In one embodiment, vasculature segmentation circuitry 355 is configured to identify a center line of the 3D segmented vasculature using a fast marching approach. Vasculature segmentation circuitry 355 may be configured identify a centerline of a vessel and branching points associated with the vessel. FIG. 2 represents detected centerlines 220 associated with a nodule 210 that is similar to nodule 110. In another embodiment, vasculature segmentation circuitry 355 is configured to identify a center line of the 3D segmented vasculature using a medial axis based skeletonization approach.

QVT feature extraction circuitry 357 is configured to extract a set of QVT features from the radiological image. QVT extraction circuitry 357 extracts the set of QVT features based, at least in part, on the center line. The set of QVT features includes a maximum curvature of vessels branch feature, a standard deviation of vessel torsion feature, and a mean curvature feature. In another embodiment, the set of QVT features may include other, different tortuosity features. For example, in one embodiment in which the radiological image is a post-treatment CT image, the set of QVT features may include a mean of torsion segments corresponding to a vessel branch, a mean of the maximum of the maximum curvature of segments associated with a vessel branch, a feature from a histogram of constituent segments curvature, and a feature from a histogram of constituent points curvature.

In one embodiment, QVT feature extraction circuitry 357 calculates the torsion for a vessel segment using a distance metric. The torsion of a vessel segment is defined as 1−(Distance/Length) where distance is the Euclidean distance of the start and end point of the segment, and where length is the number of voxels along the vessel segment. QVT feature extraction circuitry 357 also extracts the curvature of a vessel segment. Curvature at a voxel of a vessel segment is proportional to the inverse of an osculating circle's radius. The osculating circle is fitted to a collection of three neighboring points along the centerline of a vessel. For a plurality of points along the center line of a vessel, QVT feature extraction circuitry 357 fits a circle to compute the curvature of a specific point. QVT feature extraction circuitry 357 then computes mean and standard deviation of the curvature for points along the vessel. QVT feature extraction circuitry 357 may also capture branching statistics associated with the vessel. In one embodiment, QVT feature extraction circuitry 357 may provide the set of QVT features to classification circuitry 359 or memory 320.

The set of set of QVT features includes tortuosity features that describe vessels associated with the nodule. Example embodiments use a set of tortuosity features to quantify a measure of aggressiveness or irregularity in vessels associated with a nodule, tumor, or region of tissue associated with a nodule or tumor. The set of tortuosity features may include the mean of torsion of a vessel segment, or the standard deviation of torsion of a vessel segment. The set of tortuosity features may also include the mean and standard deviation of the mean curvature of a group of vessel segments. The set of tortuosity features may also include the mean and standard deviation of a vessel segment curvature and a total vessel segment length. The set of tortuosity features may also include branching statistics associated with the vessel. For example, example embodiments may extract a torsion feature, a statistics of standard deviation of branches curvature feature, a statistics of average curvature of branches feature, a statistic of maximum curvature of the branches feature, a branching count of a vasculature feature, a normalized volume of a vasculature feature, a volume feature, a histogram of torsion feature, or a histogram of curvature feature. Other tortuosity features may be extracted.

Classification circuitry 359 is configured to compute a probability that the region of tissue will respond to immunotherapy. Classification circuitry 359 computes the probability based, at least in part, on the set of QVT features. In one embodiment, classification circuitry 359 may receive the set of QVT features from QVT feature extraction circuitry 357, or may retrieve the set of QVT features from memory 320. Classification circuitry 359 is further configured to generate a classification that the region of tissue is a responder or a non-responder. Classification circuitry 359 generates the classification based, at least in part, on the probability.

In one embodiment, classification circuitry 359 includes a machine learning classifier. In one embodiment, the machine learning classifier is a support vector machine (SVM) classifier trained on a set of QVT training features selected from a set of QVT candidate features extracted from a set of training images. In this embodiment, the set of training images includes a set of CT images of a region of tissue demonstrating NSCLC. The set of CT images includes a first subset of CT images representing a region of tissue demonstrating NSCLC classified as a responder to immunotherapy, and a second, disjoint subset of CT images representing a region of tissue demonstrating NSCLC classified as a non-responder to immunotherapy. The set of QVT training features are selected based on a univariate analysis and a multivariate analysis of a member of the set of QVT candidate features' ability to discriminate a region of tissue represented in the set of training images as a responder to immunotherapy. In one embodiment, the set of QVT training features are selected using a Minimum Redundancy Maximum Relevance (mRMR) feature selection approach. In one embodiment, the machine learning classifier is a quadratic discriminant analysis (QDA) classifier trained on a set of eight QVT training features selected using an mRMR feature selection approach from a set of 35 QVT candidate features extracted from a set of 23 training images. In this embodiment using a QDA classifier, responders are discriminated from non-responders by an AUC of at least 0.74. While 35 QVT candidate features extracted from a set of 23 training images are described, other numbers of QVT candidate features or training images may be employed.

In one embodiment, computing the probability that the region of tissue will respond to immunotherapy includes computing the probability that the region of tissue will respond to nivolumab immunotherapy. In another embodiment, the probability that the region of tissue will respond to pembrolizumab immunotherapy, or atezolizumab immunotherapy may be computed. In another embodiment, the probability that the region of tissue will respond to other, different types of immunotherapy may be computed. In one embodiment the set of CT images includes a first subset of CT images representing a region of tissue demonstrating NSCLC classified as a responder to nivolumab immunotherapy, pembrolizumab immunotherapy, or atezolizumab immunotherapy, and a second, disjoint subset of CT images representing a region of tissue demonstrating NSCLC classified as a non-responder to nivolumab immunotherapy, pembrolizumab immunotherapy, or atezolizumab immunotherapy respectively.

Figure 4:
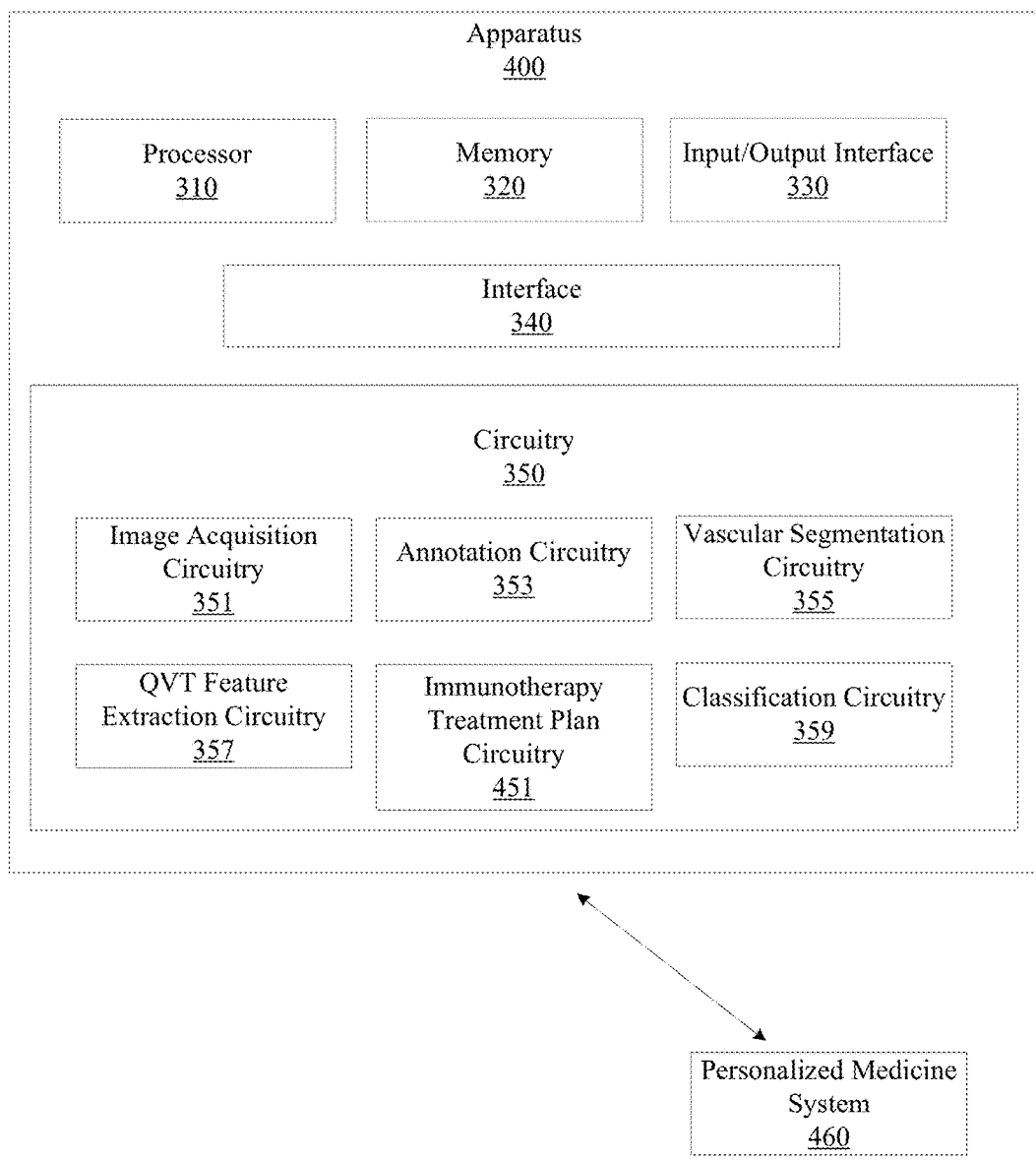
FIG. 4 illustrates an example apparatus for predicting response to immunotherapy.

FIG. 4 illustrates an immunotherapy response prediction apparatus 400 that is similar to immunotherapy response prediction apparatus 300, but that includes additional elements and details. Immunotherapy response prediction apparatus 400 includes immunotherapy treatment plan circuitry 451. Immunotherapy treatment plan circuitry 451 is configured to generate an NSCLC immunotherapy treatment plan based, at least in part, on the classification and at least one of the probability, the set QVT features, or the radiological image. The NSCLC immunotherapy treatment plan defines an immunotherapy drug or agent dosage amount and an immunotherapy drug or agent dosage schedule.

In one embodiment, immunotherapy treatment plan circuitry 451 is further configured to provide the NSCLC immunotherapy treatment plan and at least one of the classification, the probability, the set of QVT features, or the radiological image to a personalized medicine system 460. In this embodiment, immunotherapy treatment plan circuitry 451 is further configured to control the personalized medicine system 460 to display the NSCLC immunotherapy treatment plan and at least one of the classification, the probability, the set of QVT features, or the radiological image. Providing the NSCLC immunotherapy treatment plan and at least one of the classification, the probability, the set of QVT features, or the radiological image to personalized medicine system 460 may include retrieving electronic data from a computer memory, including but not limited to memory 320, receiving a computer file over a computer network, or other computer or electronic based action. Controlling the personalized medicine system 460 to display the NSCLC immunotherapy treatment plan and at least one of the classification, the probability, the set of QVT features, or the radiological image may include retrieving electronic data from a computer memory, including but not limited to memory 320, receiving a computer file over a computer network, or other computer or electronic based action.

In one embodiment, immunotherapy treatment plan circuitry 451 may be configured to control an immunotherapy dosage system to administer a dosage of an immunotherapy agent or drug defined by the NSCLC immunotherapy plan to a patient represented in the radiological image. Immunotherapy treatment plan circuitry 451 may be configured to control the immunotherapy dosage system to administer the dosage by an intravenous infusion, by an intravesical infusion, or by other techniques.

In one embodiment of immunotherapy response prediction apparatus 300 or immunotherapy response prediction apparatus 400, the set of circuitry 350 also includes display circuitry. The display circuitry is configured to display the radiological image, the classification, the segmented 3D vasculature, the center line, the nodule, or the QVT features, on a computer monitor, a smartphone display, a tablet display, or other displays. Displaying the radiological image, the classification, the nodule, the segmented 3D vasculature, the center line, or the QVT features may also include printing the radiological image, the classification, the nodule, the segmented 3D vasculature, the center line, or the QVT features. The display circuitry may also be configured to display an image of the region of tissue demonstrating the nodule. The image of the region of tissue demonstrating the nodule may include a delineated or segmented representation of the nodule, vessels, or 3D segmented vasculature associated with the nodule. By displaying the radiological image, the classification, the nodule, the QVT features, the nodule, vessels, or 3D segmented vasculature associated with the nodule, example apparatus provide a timely and intuitive way for a human radiologist to more accurately classify pathologies demonstrated by a patient, thus improving on conventional approaches to predicting response to immunotherapy.

Figure 5:
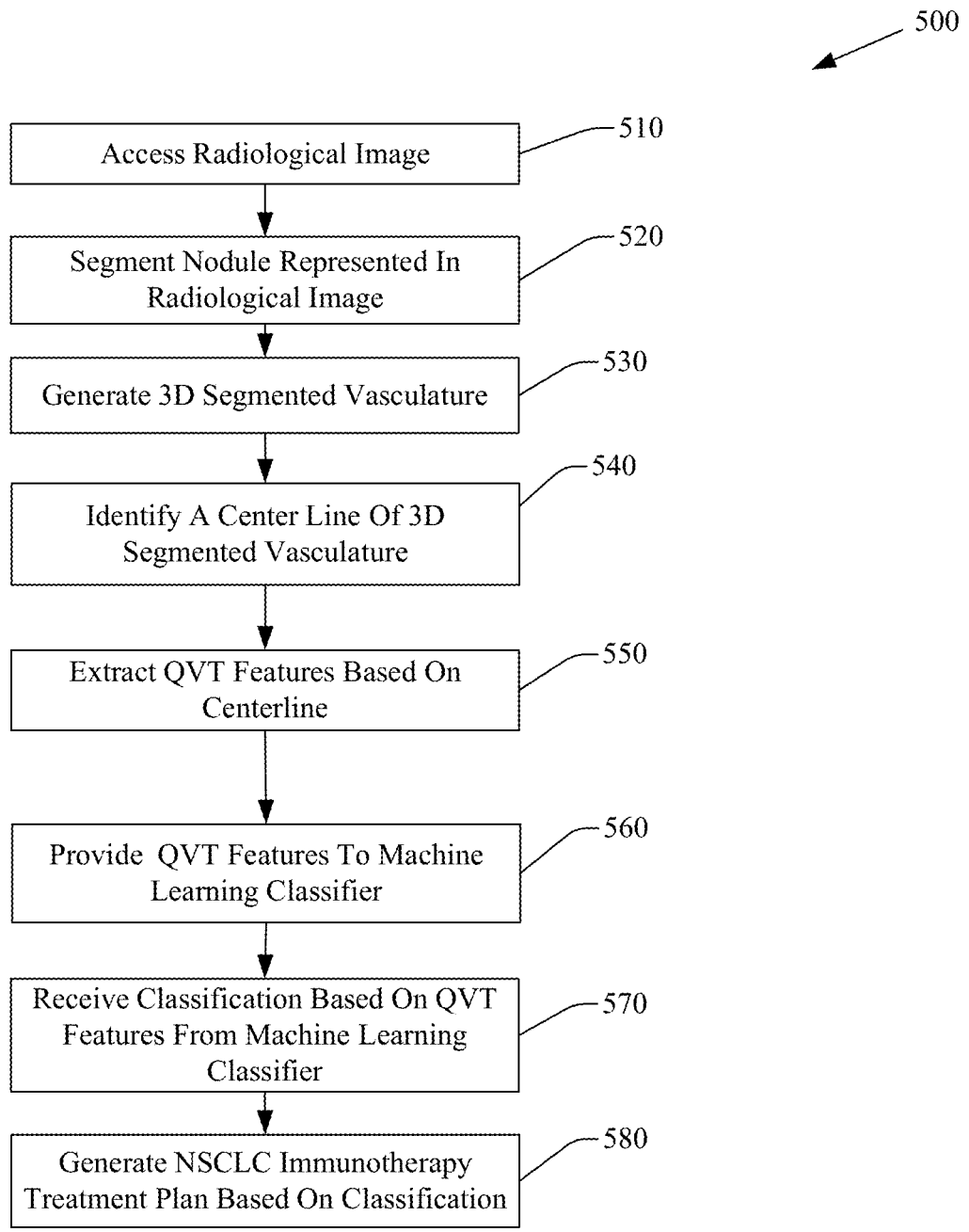
FIG. 5 illustrates a flow diagram of an example method for predicting response to immunotherapy.

FIG. 5 illustrates an example method 500 for predicting NSCLC patient response to immunotherapy. Method 500 includes, at 510, accessing a radiological image of a region of tissue demonstrating NSCLC pathology. Accessing the radiological image includes accessing a baseline pre-treatment CT image of the region of tissue, or a post-treatment CT image of the region of tissue. Accessing the radiological image may include retrieving electronic data from a computer memory, receiving a computer file over a computer network, or other computer or electronic based action. In one embodiment, the radiological image is a 1 mm to 5 mm thick, no-contrast chest CT image. In one embodiment, the number of slices per scan may range from 126 to 385, and a slice may have an XY planar resolution of 512 pixels by 512 pixels, with a 16 bit gray scale resolution indicated in HU. In another embodiment, other image types, modalities, resolutions, scales, slices per scan, or image dimensions may be used. The radiological image has a plurality of voxels, a voxel having an intensity.

Method 500 also includes, at 520, segmenting a nodule represented in the image by extracting a nodule boundary from the image. In one embodiment, segmenting the nodule represented in the image includes segmenting the nodule using a SEGvAC approach. In another embodiment, the nodule may be segmented using a heuristic threshold approach, threshold based segmentation, a deformable boundary model, an active-appearance model, an active shape model, a graph based model including Markov random fields (MRF), a min-max cut approach, or other image segmentation approach. In another embodiment, the nodule may be manually segmented using, for example, a 3D Slicer software tool. Method 500 may further include, at 520, defining a volume of interest associated with the nodule. The volume of interest may be in the nodule, or the volume interest may include a region associated with the nodule. For example, the volume of interest may include a spherical volume extending a threshold distance from the centroid of the nodule. In one embodiment, the volume of interest may be defined as a function of a property of the nodule. The property of the nodule may include, for example, a diameter, a radius, a perimeter, an area, a volume, or other property of the nodule.

Embodiments described herein may include removing pixels having less than a threshold level of HU from the radiological image of the nodule, or from the volume of interest. Lung parenchyma have HU values of approximately −500. In one embodiment, the threshold level is −900 HU. Removing pixels having less than a threshold level of HU from the volume of interest or the nodule facilitates radiomic analysis of the volume of interest or the nodule by removing confounding information from the image being analyzed, or by reducing the amount of computational resources required to extract features from the volume of interest or the nodule compared to conventional approaches. For example, pixels representing air, which has an HU value of approximately −1000, may be removed from the image. Other tissue, including bone, may also be removed. For example, pixels representing cancellous bone (+700HU) or cortical bone (+3000 HU) may be removed.

Method 500 also includes, at 530, generating a 3D segmented vasculature by segmenting a vessel associated with the nodule from the nodule. In one embodiment, segmenting the vessel from the nodule includes segmenting the vessel from the nodule using a 3D click and grow approach. In another embodiment, segmenting the vessel from the nodule includes segmenting the vessel using an atlas based approach, a watershed based segmentation approach, or an active contour based method Method 500 also includes, at 540, identifying a center line of the 3D segmented vasculature. In one embodiment, the center line is identified using a fast marching approach. In another embodiment, the center line is identified using a medial axis based skeletonization approach.

Method 500 also includes, at 550, extracting a set of QVT features from the 3D segmented vasculature. The set of QVT features may be extracted based, at least in part, on the center line. In one embodiment, the set of QVT features includes a maximum curvature of vessels branch feature, a standard deviation of vessel torsion feature, and a mean curvature feature. In another embodiment, the set of QVT features includes other, different tortuosity features. For example, in one embodiment, the set of QVT features may include a mean of torsion segments corresponding to a vessel branch, a mean of the maximum of the maximum curvature of segments associated with a vessel branch, a feature from a histogram of constituent segments curvature, and a feature from a histogram of constituent points curvature.

Method 500 also includes, at 560, providing the set of QVT features to a machine learning classifier. Providing the set of QVT features to machine learning classifier may include retrieving electronic data from a computer memory, receiving a computer file over a computer network, or other computer or electronic based action.

In one embodiment, the machine learning classifier is an SVM classifier. The SVM classifier is trained on a set of QVT training features selected from a set of QVT candidate features. The set of QVT candidate features are extracted from a set of training images. The set of training images includes a set of CT images of a region of tissue demonstrating NSCLC. The of CT images includes a first subset of CT images representing a region of tissue demonstrating NSCLC classified as a responder to immunotherapy, and a second, disjoint subset of CT images representing a region of tissue demonstrating NSCLC classified as a non-responder to immunotherapy. In another embodiment, the machine learning classifier is a QDA classifier or other type of machine learning classifier trained on the set of QVT training features.

Method 500 also includes, at 570, receiving, from the machine learning classifier, a classification of the region of tissue. The machine learning classifier may generate the classification by classifying the region of tissue as a responder or non-responder. The classification is based on a probability computed by the machine learning classifier that the region of tissue will respond to immunotherapy based, at least in part, on the set of QVT features. The classification may classify the region of tissue as a responder to nivolumab immunotherapy, pembrolizumab immunotherapy, atezolizumab immunotherapy, or other type of immunotherapy. The SVM classifier classifies the nodule represented in a baseline pre-treatment image with an accuracy of at least 0.72 AUC.

Method 500 further includes, at 580, generating an NSCLC immunotherapy treatment plan. Method 500 may generate the NSCLC treatment plan based, at least in part, on the classification and at least one of the probability, the set of QVT features, or the radiological image. The immunotherapy treatment plan includes an immunotherapy dosage and an immunotherapy schedule. For example, the NSCLC immunotherapy treatment plan may define a nivolumab dosage amount and schedule for a patient identified as a responder, while for a non-responder, other treatments may be suggested. In one embodiment, method 500 further includes controlling an immunotherapy system to administer a dosage of an immunotherapy agent to a patient based, at least in part, on the immunotherapy treatment plan. In one embodiment, method 500 may control an immunotherapy dosage system to administer a dosage of an immunotherapy agent defined by the NSCLC immunotherapy plan by an intravenous infusion, or by an intravesical infusion.

While FIG. 5 illustrates various actions occurring in serial, it is to be appreciated that various actions illustrated in FIG. 5 could occur substantially in parallel. By way of illustration, a first process could delineate a nodule in a CT image, a second process could segment a 3D vasculature in CT image, and a third process could extract tortuosity features from the CT image. While three processes are described, it is to be appreciated that a greater or lesser number of processes could be employed and that lightweight processes, regular processes, threads, and other approaches could be employed.

One embodiment includes a computer-readable storage device storing processor-executable instructions that, in response to execution, cause a processor to perform operations. A processor may include circuitry such as, but not limited to, one or more single-core or multi-core processors. The processor(s) may include any combination of general-purpose processors and dedicated processors (e.g., graphics processors, application processors, etc.). The processor(s) may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The operations include accessing a radiological image of a region of tissue demonstrating non-small cell lung cancer (NSCLC). In one embodiment, the radiological image is a baseline pre-immunotherapy treatment image, or a post-immunotherapy treatment image. Accessing the radiological image may include retrieving electronic data from a computer memory, receiving a computer file over a computer network, or other computer or electronic based action.

The operations also include segmenting a lung region from surrounding anatomy in the region of tissue represented in the radiological image. In one embodiment, the operations include using a multi-threshold based approach or a heuristic threshold based approach to segment the lung region.

The operations also include segmenting a nodule from the lung region by defining a nodule boundary. In one embodiment, segmenting the nodule represented in the image includes segmenting the nodule using a SEGvAC approach. In another embodiment, the nodule may be segmented using a heuristic threshold approach, threshold based segmentation, a deformable boundary model, an active-appearance model, an active shape model, a graph based model including Markov random fields (MRF), a min-max cut approach, or other image segmentation approach.

The operations also include generating a 3D segmented vasculature by segmenting a vessel from the nodule. In one embodiment, segmenting the vessel from the nodule includes segmenting the vessel from the nodule using a 3D click and grow approach.

The operations also include identifying a center line of the 3D segmented vasculature using a fast marching approach. In another embodiment, the operations include identifying the center line using a medial axis based skeletonization approach.

The operations also include extracting a set of QVT features from the 3D segmented vasculature based, at least in part, on the center line. In one embodiment, the set of QVT features includes a maximum curvature of vessels branch feature, a standard deviation of vessel torsion feature, and a mean curvature feature. In another embodiment, the set of QVT features includes include a mean of torsion segments corresponding to a vessel branch, a mean of the maximum of the maximum curvature of segments associated with a vessel branch, a feature from a histogram of constituent segments curvature, and a feature from a histogram of constituent points curvature.

The operations also include providing the set of QVT features to a machine learning classifier. In one embodiment, the machine learning classifier is an SVM classifier. In another embodiment, the machine learning classifier is a QDA classifier.

The operations also include receiving, from the machine learning classifier, a probability that the region of tissue will respond to immunotherapy. The machine learning classifier computes the probability based, at least in part, on the set of QVT features. In one embodiment, immunotherapy includes nivolumab immunotherapy, pembrolizumab immunotherapy, atezolizumab immunotherapy, or other type of immunotherapy.

The operations further include generating a classification of the region of tissue represented in the radiological image by classifying the region of tissue as a responder or non-responder based, at least in part, on the probability.

In one embodiment, the operations further include generating an NSCLC immunotherapy treatment plan. The operations may include generating the NSCLC treatment plan based, at least in part, on the classification and at least one of the probability, the set of QVT features, or the radiological image. In this embodiment, the operations may further include controlling an immunotherapy system to administer an immunotherapy agent to a patient based, at least in part, on the immunotherapy treatment plan.

Figure 7:
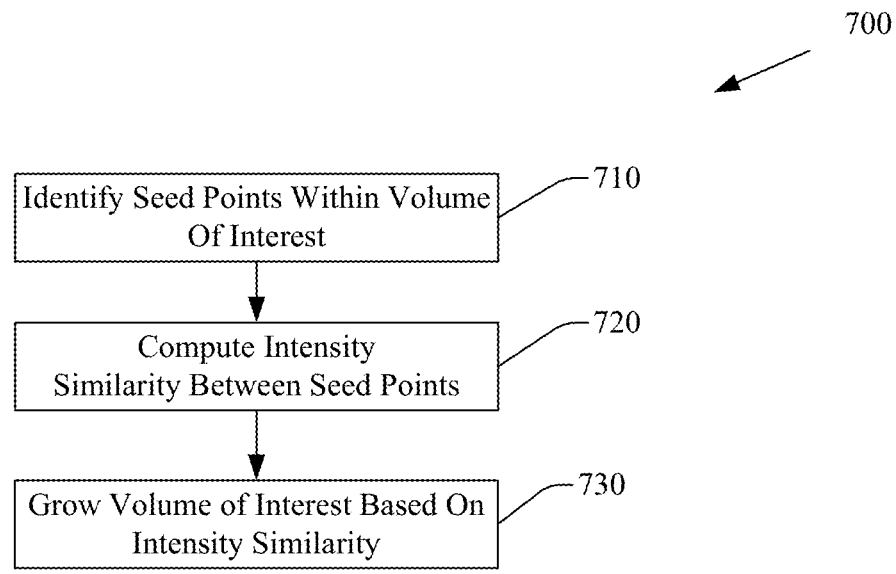
FIG. 7 illustrates a flow diagram of an example method for segmenting a vessel represented in a radiological image using a 3D click and grow approach.

FIG. 7 illustrates a method 700 for segmenting a vessel represented in a radiological image using a 3D click and grow approach. Method 700 is suitable for implementation with apparatus 300, apparatus 400, method 500, or other embodiments described herein. Method 700 includes, at 710, identifying a seed point within a volume of interest. A seed point may be a member of a plurality of seed points. A seed point has an intensity. The volume of interest may be in the nodule, or the volume interest may include a region associated with the nodule. For example, the volume of interest may include a spherical volume extending a threshold distance from the centroid of the nodule. The volume of interest may be defined using other approaches described herein.

Method 700 also includes, at 720, computing an intensity similarity. The intensity similarity may represent the similarity between an intensity of a first member of the plurality of seed points, and an intensity of a second, different member of the plurality of seed points. The intensity similarity may represent the similarity of intensity between other, different numbers of seed points.

Method 700 also includes, at 730, growing the volume of interest. Example embodiments may grow the volume of interest using a 3D region growing approach. The 3D region growing approach may be based, at least in part, on the intensity similarity.

Embodiments described herein facilitate more accurate characterization of nodules found in CT images than conventional approaches. Example embodiments thus improve on conventional methods by predicting response to immunotherapy with greater accuracy and with less subjective variability than conventional methods. Example methods, apparatus, and other embodiments therefore facilitate more judicious application of immunotherapy, biopsies, or surgical resection in a population undergoing CT screening for lung cancer.

Using a more appropriately determined and applied treatment may lead to less therapeutics being required for a patient or may lead to avoiding or delaying a biopsy, a resection, or other invasive procedure. When regions of cancerous tissue, including nodules detected in CT scans, are more quickly and more accurately classified, patients with poorer prognoses may receive a higher proportion of scarce resources (e.g., therapeutics, physician time and attention, hospital beds) while those with better prognoses may be spared unnecessary treatment, which in turn spares unnecessary expenditures and resource consumption. Example methods and apparatus may thus have the real-world, quantifiable effect of improving patient outcomes.

Methods, apparatus, and other embodiments described herein are described with reference to the drawings in which like reference numerals are used to refer to like elements throughout, and where the illustrated structures are not necessarily drawn to scale. Embodiments are to cover all modifications, equivalents, and alternatives falling within the scope of the invention. In the figures, the thicknesses of lines, layers and/or regions may be exaggerated for clarity. Nothing in this detailed description (or drawings included herewith) is admitted as prior art.

Like numbers refer to like or similar elements throughout the description of the figures. When an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In one example, a method may be implemented as computer executable instructions. Thus, in one example, a computer-readable storage medium may store computer executable instructions that if executed by a machine (e.g., computer) cause the machine to perform methods described or claimed herein including method 500. While executable instructions associated with the listed methods are described as being stored on a computer-readable storage device or medium, it is to be appreciated that executable instructions associated with other example methods described or claimed herein may also be stored on a computer-readable storage device or medium. In different embodiments the example operations or methods described herein may be triggered in different ways. In one embodiment, a method or operation may be triggered manually by a user. In another example, a method or operation may be triggered automatically.

Figure 6:
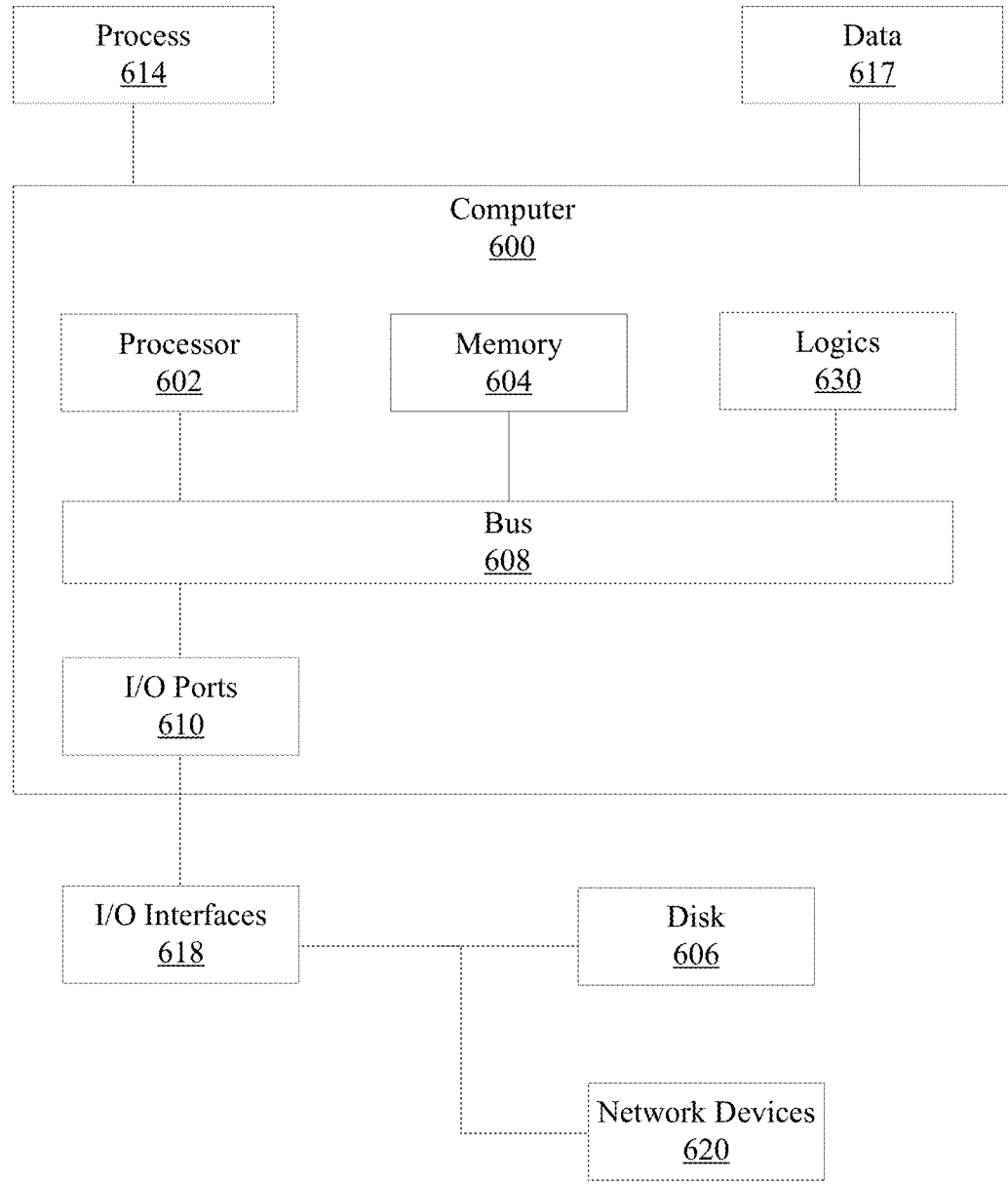
FIG. 6 illustrates an example computer in which example methods and apparatus may operate.

FIG. 6 illustrates an example computer 600 in which example methods illustrated herein can operate and in which example operations, circuits or logics may be implemented. In different examples, computer 600 may be part of a CT system, may be operably connectable to a CT system, may be part of an MRI system, or may be part of a CADx system.

Computer 600 includes a processor 602, a memory 604, and input/output ports 610 operably connected by a bus 608. In one example, computer 600 may include a set of logics 630 that perform a method of predicting response to NSCLC. Thus, the set of logics 630, whether implemented in computer 600 as hardware, firmware, software, and/or a combination thereof may provide means (e.g., hardware, software) for predicting response to immunotherapy. In different examples, the set of logics 630 may be permanently and/or removably attached to computer 600. In one embodiment, the functionality associated with the set of logics 630 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 630 are implemented as ASICs or SOCs.

Processor 602 can be a variety of various processors including dual microprocessor and other multi-processor architectures. Memory 604 can include volatile memory and/or non-volatile memory. A disk 606 may be operably connected to computer 600 via, for example, an input/output interface (e.g., card, device) 618 and an input/output port 610. Disk 606 may include, but is not limited to, devices like a magnetic disk drive, a tape drive, a Zip drive, a solid state device (SSD), a flash memory card, or a memory stick. Furthermore, disk 606 may include optical drives like a CD-ROM or a digital video ROM drive (DVD ROM). Memory 604 can store processes 614 or data 617, for example. Disk 606 or memory 604 can store an operating system that controls and allocates resources of computer 600.

Bus 608 can be a single internal bus interconnect architecture or other bus or mesh architectures. While a single bus is illustrated, it is to be appreciated that computer 600 may communicate with various devices, logics, and peripherals using other busses that are not illustrated (e.g., PCIE, SATA, Infiniband, 1394, USB, Ethernet).

Computer 600 may interact with input/output devices via I/O interfaces 618 and input/output ports 610. Input/output devices can include, but are not limited to, digital whole slide scanners, a CT apparatus, an MRI apparatus, an optical microscope, a keyboard, a microphone, a pointing and selection device, cameras, video cards, displays, disk 606, network devices 620, or other devices. Input/output ports 610 can include but are not limited to, serial ports, parallel ports, or USB ports.

Computer 600 may operate in a network environment and thus may be connected to network devices 620 via I/O interfaces 618 or I/O ports 610. Through the network devices 620, computer 600 may interact with a network. Through the network, computer 600 may be logically connected to remote computers. The networks with which computer 600 may interact include, but are not limited to, a local area network (LAN), a wide area network (WAN), the cloud, or other networks.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a solid state device (SSD), a memory stick, a data storage device, and other media from which a computer, a processor or other electronic device can read.

"Circuit" or "circuitry", as used herein, includes but is not limited to hardware, firmware, software in execution on a machine, or combinations of each to perform a function(s) or an action(s), or to cause a function or action from another circuit, method, or system. Circuitry may include a software controlled microprocessor, a discrete logic (e.g., ASIC), an analog circuit, a digital circuit, a programmed logic device, a memory device containing instructions, and other physical devices. Circuitry may include one or more gates, combinations of gates, or other circuit components. Where multiple logical circuits are described, it may be possible to incorporate the multiple circuits into one physical logic or circuit. Similarly, where a single logical circuit is described, it may be possible to distribute that single circuit between multiple logics or circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. An immunotherapy response prediction apparatus, configured to generate a classification of a region of tissue demonstrating non-small cell lung cancer (NSCLC) based on a set of quantitative vessel tortuosity (QVT) features extracted from a radiological image of the region of tissue, the apparatus comprising:
   a processor;
   a memory;
   an input/output interface;
   a set of circuitry; and
   an interface to connect the processor, the memory, the input/output interface and the set of circuitry, where the set of circuitry includes:
      image acquisition circuitry configured to access a radiological image of a region of tissue demonstrating NSCLC;
      annotation circuitry configured to:
         segment a lung region from surrounding anatomy in the region of tissue represented in the radiological image;
         segment a nodule from the lung region by defining a nodule boundary;
      vascular segmentation circuitry configured to:
         generate a three dimensional (3D) segmented vasculature by segmenting a vessel associated with the nodule from the nodule;
         identify a center line of the 3D segmented vasculature;

QVT feature extraction circuitry configured to extract a set of QVT features from the radiological image based, at least in part, on the center line; and classification circuitry configured to:
compute a probability that the region of tissue will respond to immunotherapy based, at least in part, on the set of QVT features; and
generate a classification of the region of tissue as a responder or a non-responder based, at least in part, on the probability.

2. The immunotherapy response prediction apparatus of claim 1, where accessing the radiological image comprises accessing a computed tomography (CT) image of a region of lung tissue, where the CT image is a no-contrast chest CT image.

3. The immunotherapy response prediction apparatus of claim 2, where the CT image is a baseline pre-treatment CT image.

4. The immunotherapy response prediction apparatus of claim 2, where the CT image is a post-treatment CT image acquired at least two weeks after administration of immunotherapy treatment to a patient represented in the image.

5. The immunotherapy response prediction apparatus of claim 1, where the annotation circuitry is configured to segment the lung region from surrounding anatomy in the region of tissue represented in the radiological image by distinguishing the lung region from the surrounding anatomy using a multi-threshold based approach or a heuristic threshold based approach.

6. The immunotherapy response prediction apparatus of claim 1, where the annotation circuitry is configured to segment the nodule from the lung region by defining the nodule boundary by:
distinguishing nodule tissue in the radiological image from the background of the radiological image using a spectral embedding gradient vector flow active contour (SEGvAC) approach; or
distinguishing nodule tissue in the radiological image from the background of the radiological image using a heuristic threshold approach, a deformable boundary model, an active-appearance model, an active shape model, a Markov random fields (MRF) graph-based model, or a min-max cut approach.

7. The immunotherapy response prediction apparatus of claim 1, where the vascular segmentation circuitry is configured to segment the vessel from the nodule using a three dimensional (3D) click and grow approach.

8. The immunotherapy response prediction apparatus of claim 7, where the vascular segmentation circuitry is configured to segment the vessel from the nodule using the 3D click and grow approach by:
identifying a plurality of seed points within a volume of interest, where a member of the plurality of seed points has an intensity, where the volume of interest is in the nodule;
computing an intensity similarity between a first member of the plurality of seed points and a second, different member of the plurality of seed points; and
growing the volume of interest using a 3D region growing approach based, at least in part, on the intensity similarity.

9. The immunotherapy response prediction apparatus of claim 1, where the vascular segmentation circuitry is configured to identify the center line of the 3D segmented vasculature using a fast marching approach.

10. The immunotherapy response prediction apparatus of claim 1, where the set of QVT features includes a maximum curvature of vessels branch feature, a standard deviation of vessel torsion feature, and a mean curvature feature.

11. The immunotherapy response prediction apparatus of claim 1, where the classification circuitry comprises a machine learning classifier.

12. The immunotherapy response prediction apparatus of claim 11, where the machine learning classifier is a support vector machine (SVM) classifier trained on a set of QVT training features selected from a set of QVT candidate features extracted from a set of training images,
where the set of training images includes a set of computed tomography (CT) images of a region of tissue demonstrating NSCLC, where the set of CT images includes a first subset of CT images representing a region of tissue demonstrating NSCLC classified as a responder to immunotherapy, and a second, disjoint subset of CT images representing a region of tissue demonstrating NSCLC classified as a non-responder to immunotherapy, and
where the set of QVT training features are selected based on a univariate analysis and a multivariate analysis of the ability of a member of the set of QVT candidate features to discriminate a region of tissue represented in the set of training images as a responder to immunotherapy.

13. The immunotherapy response prediction apparatus of claim 1, where computing the probability that the region of tissue will respond to immunotherapy based, at least in part, on the set of QVT features, includes computing the probability that the region of tissue will respond to nivolumab immunotherapy, pembrolizumab immunotherapy, or atezolizumab immunotherapy.

14. The immunotherapy response prediction apparatus of claim 1, further comprising immunotherapy treatment plan circuitry configured to:
generate an NSCLC immunotherapy treatment plan based, at least in part, on the classification and at least one of the probability, the set QVT features, or the radiological image, where the NSCLC immunotherapy treatment plan defines an immunotherapy dosage amount and an immunotherapy dosage schedule.

15. The immunotherapy response prediction apparatus of claim 14, where the immunotherapy treatment plan circuitry is further configured to:
provide the NSCLC immunotherapy treatment plan and at least one of the classification, the probability, the set of QVT features, or the radiological image to a personalized medicine system; and
control the personalized medicine system to display the NSCLC immunotherapy treatment plan and at least one of the classification, the probability, the set of QVT features, or the radiological image.

16. A non-transitory computer-readable storage device storing computer executable instructions that when executed by a computer control the computer to perform a method for predicting non-small cell lung cancer (NSCLC) patient response to immunotherapy, the method comprising:
accessing a radiological image of a region of tissue demonstrating NSCLC pathology, where accessing the radiological image includes accessing a baseline pre-treatment computed tomography (CT) image of the region of tissue, or a post-treatment CT image of the region of tissue;
segmenting a nodule in the image by extracting a nodule boundary from the image;

generating a three dimensional (3D) segmented vasculature by segmenting a vessel associated with the nodule from the nodule;

identifying a center line of the 3D segmented vasculature;

extracting a set of quantitative vessel tortuosity (QVT) features from the 3D segmented vasculature based, at least in part, on the center line;

providing the set of QVT features to a machine learning classifier;

receiving, from the machine learning classifier, a classification of the region of tissue as a responder or non-responder, where the classification is based on a probability computed by the machine learning classifier that the region of tissue will respond to immunotherapy based, at least in part, on the set of QVT features; and generating an NSCLC immunotherapy treatment plan based, at least in part, on the classification and at least one of the probability, the set of QVT features, or the radiological image.

17. The non-transitory computer-readable storage device of claim 16, where segmenting the nodule in the image includes segmenting the nodule using a spectral embedding active contour (SEGvAC) approach, a heuristic threshold approach, threshold based segmentation, a deformable boundary model, an active-appearance model, an active shape model, a Markov random fields (MRF) graph-based model, or a min-max cut approach, and where segmenting the vessel from the nodule includes segmenting the vessel from the nodule using a 3D click and grow approach.

18. The non-transitory computer-readable storage device of claim 16 where the set of QVT features includes a maximum curvature of vessels branch feature, a standard deviation of vessel torsion feature, and a mean curvature feature.

19. The non-transitory computer-readable storage device of claim 16, where the machine learning classifier is a support vector machine (SVM) classifier trained on a set of QVT training features selected from a set of QVT candidate features extracted from a set of training images, where the set of training images includes a set of CT images of a region of tissue demonstrating NSCLC, where the set of CT images includes a first subset of CT images representing a region of tissue demonstrating NSCLC classified as a responder to immunotherapy, and a second, disjoint subset of CT images representing a region of tissue demonstrating NSCLC classified as a non-responder to immunotherapy.

20. A computer-readable storage device storing processor-executable instructions that, in response to execution, cause a processor to perform operations comprising:

accessing a radiological image of a region of tissue demonstrating non-small cell lung cancer (NSCLC), where the radiological image is a baseline pre-immunotherapy treatment image, or a post-immunotherapy treatment image;

segmenting a lung region from surrounding anatomy in the region of tissue represented in the radiological image;

segmenting a nodule from the lung region by defining a nodule boundary;

generating a three dimensional (3D) segmented vasculature by segmenting a vessel from the nodule;

identifying a center line of the 3D segmented vasculature using a fast marching approach;

extracting a set of quantitative vessel tortuosity (QVT) features from the 3D segmented vasculature based, at least in part, on the center line;

providing the set of QVT features to a support vector machine (SVM) classifier;

receiving, from the SVM classifier, a probability that the region of tissue will respond to immunotherapy based, at least in part, on the set of QVT features; and generating a classification by classifying the region of tissue as a responder or non-responder based, at least in part, on the probability.

* * * * *

UNITED STATES PATENT AND TRADEMARK OFFICE
CERTIFICATE OF CORRECTION

PATENT NO. : 10,492,723 B2
APPLICATION NO. : 15/883649
DATED : December 3, 2019
INVENTOR(S) : Anant Madabhushi et al.

It is certified that error appears in the above-identified patent and that said Letters Patent is hereby corrected as shown below:

In the Specification

Column 1, Lines 14 through 27; please replace "The invention was made with government support under the National Cancer Institute of the National Institutes of Health under award numbers 1U24CA199374-01, R01CA202752-01A1, R01CA208236-01A1, R21CA179327-01, R21CA195152-01, the National Institute of Diabetes and Digestive and Kidney Diseases under award number R01DK098503-02, National Center for Research Resources under award number 1 C06 RR12463-01, the DOD Prostate Cancer Synergistic Idea Development Award (PC120857), the DOD Lung Cancer Idea Development New Investigator Award (LC130463), the DOD Prostate Cancer Idea Development Award, and the DOD Peer Reviewed Cancer Research Program W81XWH-16-1-0329. The government has certain rights in the invention." with --This invention was made with government support under grants CA179327, CA195152, DK098503, CA199374, CA202752, CA208236, and RR012463 awarded by the National Institutes of Health; and grants W81XWH-16-1-0329, W81XWH-14-1-0323, W81XWH-13-1-0418, and W81XWH-15-1-0558 awarded by the Department of Defense. The government has certain rights in the invention.--

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*